(12) United States Patent
Wang et al.

(10) Patent No.: US 8,431,011 B2
(45) Date of Patent: Apr. 30, 2013

(54) METHOD FOR AUTOMATICALLY AND RAPIDLY DISTINGUISHING BETWEEN CONTROL AND SAMPLE SOLUTIONS IN A BIOSENSOR STRIP

(75) Inventors: Yi Wang, San Ramon, CA (US); Benjamin J. Feldman, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1437 days.

(21) Appl. No.: 12/023,985

(22) Filed: Jan. 31, 2008

(65) Prior Publication Data

US 2012/0132540 A1    May 31, 2012

(51) Int. Cl.
*G01N 27/327* (2006.01)
(52) U.S. Cl.
USPC ........................................ 205/777.5; 205/792
(58) Field of Classification Search .................. 204/403.01–403.15; 205/777.5, 205/778, 792
See application file for complete search history.

(56) References Cited

U.S. PATENT DOCUMENTS

| | | | | |
|---|---|---|---|---|
| 5,120,420 A * | 6/1992 | Nankai et al. | ............. | 204/403.11 |
| 5,171,689 A * | 12/1992 | Kawaguri et al. | ........... | 204/403.1 |
| 5,262,305 A | 11/1993 | Heller et al. | | |
| 5,264,104 A | 11/1993 | Gregg et al. | | |
| 5,320,725 A | 6/1994 | Gregg et al. | | |
| 5,320,732 A * | 6/1994 | Nankai et al. | ............. | 204/403.04 |
| 5,356,786 A | 10/1994 | Heller et al. | | |
| 5,512,159 A * | 4/1996 | Yoshioka et al. | ........ | 204/403.08 |
| 5,593,852 A | 1/1997 | Heller et al. | | |
| 5,665,222 A | 9/1997 | Heller et al. | | |
| 5,672,257 A * | 9/1997 | Birch et al. | ...................... | 205/43 |
| 5,972,199 A | 10/1999 | Heller et al. | | |
| 6,103,033 A | 8/2000 | Say et al. | | |
| 6,120,676 A | 9/2000 | Heller et al. | | |
| 6,134,461 A | 10/2000 | Say et al. | | |
| 6,143,164 A | 11/2000 | Heller et al. | | |
| 6,175,752 B1 | 1/2001 | Say et al. | | |
| 6,338,790 B1 | 1/2002 | Feldman et al. | | |
| 6,645,368 B1 * | 11/2003 | Beaty et al. | .................... | 205/792 |
| 6,746,582 B2 | 6/2004 | Heller et al. | | |
| 6,824,670 B2 | 11/2004 | Tokunaga et al. | | |
| 7,122,111 B2 | 10/2006 | Tokunaga et al. | | |
| 2004/0256248 A1 * | 12/2004 | Burke et al. | .................. | 205/792 |

(Continued)

FOREIGN PATENT DOCUMENTS

| | | |
|---|---|---|
| EP | 0526226 A2 | 2/1993 |
| EP | 1593338 A1 * | 9/2005 |
| WO | WO 2006110504 A1 * | 10/2006 |

OTHER PUBLICATIONS

Bedell ("Admittance and Impedance Loci," Proc. Phys. Soc. London 14 327-336).*

Primary Examiner — Alex Noguerola
(74) *Attorney, Agent, or Firm* — Edward J. Baba; Khin Chin; Bozicevic, Field & Francis LLP

(57) ABSTRACT

The present invention is directed to electrochemical sensors and systems and methods for electrochemically sensing a particular constituent within a fluid through the use of a diagnostic test. The methods provide for automatic discrimination of sample from control or standard solutions. A device and system used to determine a constituent level within a fluid that employ such automatic sample discrimination methods or specially formulated solutions is also provided.

27 Claims, 4 Drawing Sheets

U.S. PATENT DOCUMENTS

| | | |
|---|---|---|
| 2005/0247562 A1 | 11/2005 | Tokunaga et al. |
| 2007/0135343 A1 | 6/2007 | Webb et al. |
| 2007/0149873 A1 | 6/2007 | Say et al. |
| 2007/0235347 A1 | 10/2007 | Chatelier et al. |

* cited by examiner

METHOD FOR AUTOMATICALLY AND RAPIDLY DISTINGUISHING BETWEEN CONTROL AND SAMPLE SOLUTIONS IN A BIOSENSOR STRIP

TECHNICAL FIELD

Embodiments of the claimed subject matter relate to electrochemical sensors and, more particularly, to systems and methods for electrochemically sensing a particular constituent within a fluid through the use of a diagnostic test.

BACKGROUND

In many industries it is desirable or necessary to regularly monitor the concentration of particular constituents in a fluid. A number of systems are available that analyze the constituents of bodily fluids such as blood, urine, or saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis. A number of systems that allow individuals to easily monitor their blood glucose are currently available. Such systems include electrochemical biosensors, which may comprise a test strip wherein a user applies a blood sample and a meter "reads" the test strip by correlating the current detected with glucose concentration in the blood sample.

Among the various technologies available for measuring bodily fluid constituents such as blood glucose, electrochemical technologies are particularly useful because a very small blood sample (in some cases as low as 300 nL) may suffice to perform the measurement. In amperometric electrochemical-based systems, the test strip is typically imprinted or screen-printed with working and reference electrodes. The working electrode may be coated or deposited with reagents such as enzymes that catalyze oxidation/reduction ("redox") reactions, enzyme mediators and membranes. A counter or "non-working" electrode is included, along with an optional additional "reference" electrode, also known as a "baseline" electrode. The reference electrode may be described as "non-working."

The measurement of medically relevant bodily fluid constituents may include one or more of the following enzyme reagents: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase or bilirubin oxidase. In the case of blood glucose measurements, a user typically applies a blood sample to the sample chamber, an enzyme such as glucose oxidase reacts with the glucose, and a voltage is applied across electrode one working and one non-working electrode in the sample chamber, thereby causing a redox reaction to occur. A meter then measures the resulting current and relates this to the amount of glucose in the original sample. Other systems based on coulometry or voltametry are also known. A common feature of all of these systems is the use of standard or control solutions with a known concentration of glucose to verify that the measurement apparatus is operating correctly and to ensure the accuracy of diagnostic tests.

Current technology typically requires a manual determination of whether the sample is of a control solution or a bodily fluid, such as blood. This can be problematic for several reasons; in particular, a patient's poor eyesight or lack of dexterity can make a manual selection to indicate whether the solution is a sample or control solution quite difficult. An error in this manual entry will result in an erroneous average, which can significantly affect a patient's choice of treatment options. For many patients, such manual intervention presents a substantial physical challenge. A distinct issue unrelated to the physical challenge of making such a manual adjustment, is that individuals who are responsible for showing their average glucose (a current function of most monitors) might willfully adjust their average glucose readings by using the low or normal glucose level control solution, and in this way lower, their average glucose level. Such a situation may be encountered when an individual's own actions would render the actual average glucose levels higher than desired. To further illustrate this example, when a teenager consumes food or beverages that violate a strict diet plan, he or she might be able to falsify the average glucose reading by substituting the blood sample with the low or normal glucose level control solution. Thus, manual determination of a control solution remains a substantial problem in patient care.

As stated above, electrochemical biosensor technologies typically make use of some electrode based biosensors, and a number of configurations are commonly used to support accurate measurements and meet design constraints. Specifically, such biosensors typically include at least one working electrode and at least one counter electrode, which may be on the same substrate (e.g., co-planar) or may be on different substrates (e.g., facing). Such biosensors also typically include a sample chamber to hold the sample in electrolytic contact with the working electrode. Common configurations include at least one working electrode on a first substrate and forming at least one counter or reference electrode on a second substrate. A spacer layer is disposed on either the first or second substrates. The spacer layer defines a chamber into which a sample may be drawn and held when the biosensor is completed. Chemical detection of one or more analytes may be configured on the first or second substrate in a region that will be exposed within the sample chamber when the biosensor is completed. The first and second substrates may then be brought together as a "sandwich" and spaced apart by the spacer layer with the sample chamber providing access to the at least one working electrode and the at least one counter or reference electrode.

Certain other embodiments include forming at least one working electrode on a first substrate and forming at least one counter or reference electrode on the same, first substrate. One or two additional layers may be added to define a chamber into which a sample may be drawn and held when the biosensor is completed. A "trigger" electrode may also be included to indicate when the chamber has filled with sample solution.

As provided above, the biosensor may include a working electrode and at least one counter electrode. The working electrode is the electrode through which electrons from glucose enter the biosensor. The counter electrode is where the electrons exit the sensor and return to the fluid sample. Although two electrodes is a minimum number for any electrochemical sensing device, more than two electrodes can be used. For example, a third reference, or baseline electrode may be included, which severs as a reference point to precisely set the potential (or potential to accept electrons) of the working electrode. The reference electrode may be considered a "non-working" electrode. Biosensors of the invention may include at least two non-working electrodes. In this way, biosensors of the invention can be configured to measure electron conductivity in fluid, as opposed to, or in addition to, glucose concentration. Biosensors configured to measure electron conductivity may comprise a working electrode that is temporarily disconnected or disabled. Disablement of the working electrode allows for the measurement of electron conductivity alone.

Working electrodes may be manufactured from any number of useful materials, typically made up of any combination of one or more conductive materials having in some measure desirable properties of low electrical resistance and electrochemical inertness over the potential range of the biosensor during operation. Gold, carbon, platinum, ruthenium dioxide, palladium, or other non-corroding materials are cited as particularly exemplary working electrode materials. Counter electrodes may be constructed in a manner similar to working electrode. Suitable materials for the counter/reference or reference electrode include Ag/AgCl or Ag/AgBr on a non-conducting base material or silver chloride on a silver metal base, often including a mix of multiple conducting materials, such as Ag/AgCl and carbon.

Various embodiments of methods of making biosensors include providing a sample chamber and/or measurement zone having an electrode surface area that, when filled with a sample to be tested, provides a clinically accurate analyte level reading, preferably without user intervention. In particular, the configurations disclosed here are directed toward a design that minimizes or entirely removes the need for users to manually identify control solutions or experimental solutions such as a blood sample.

Technology does exist for more automated sample discrimination, but such methods have so far been limited to situations in which the sample is blood. Such methods are problematic when the sample is not blood, and is instead urine, interstitial fluid or plasma, for example. Tokunaga et al. (U.S. Pat. Nos. 6,824,670 and 7,122,111) discloses a method of automatic sample discrimination using a discrimination function and index to distinguish a control solution from a sample solution. Importantly, this method uses the electrochemical test electrode, or working electrode, to measure current in the control and sample solutions. This technology is based on an algorithm that identifies differences in the time differential of the current measured in the control and the sample solutions. Essentially, the algorithm identifies changes in the shape of the measurement curve over time as characteristic of control or sample solutions. Such methods, however, are not entirely reliable when the sample measured is not blood.

In addition, these methods require significantly more complex measurement devices that are more expensive to develop and maintain, and the actual determination typically takes an undesirably long period of time to perform. The time differential calculations necessary to distinguish sample from control are on the order of at least several seconds. Such a long waiting period is a substantial disadvantage for users that demand glucose monitoring devices with a premium on convenience. Further, while the methods of the prior art involve a single measurement, the instantly claimed subject matter involves two measurements. The first assesses glucose concentration while the second assesses another parameter, such as, for example, electron conductivity in fluid. Embodiments of the present invention allow both of these measurements to be assessed in less time than the single measurement step of the prior art.

For example, Chatelier et al. (U.S. Application Publication No. 20070235347) describes methods for distinguishing control and sample solutions using a series of current transient measurements that enable discrimination via the measurement of the impact of endogenous redox species in blood termed interferents. This disclosure, however, does not focus on embodiments in which there is more than one non-working electrode. Nor does it describe sequential measurements in which a voltage is applied across the working electrode and a non-working electrode, followed or preceded by application of a voltage across two non-working electrodes. Provided herein is the step-wise application of a voltage across different electrode configurations resulting in two separate measurements. The magnitude of the voltage applied across the working and non-working electrode is typically low, being between about 100-300 mV. This is due to the fact that a glucose signal is relatively easy to detect. In contrast, the magnitude of the voltage applied across non-working electrodes is typically high, between about 300-500 mV. This is due to the fact that measurement of bulk solution conductivity requires a potential of relatively greater magnitude for detection.

Accordingly, the presently claimed subject matter involves applying a voltage between a working and a non-working electrode in order to quantitatively measure analyte concentration, and applying a different voltage between two non-working electrodes in order to measure another parameter, such as, for example electron conductivity. These separate measurements need not occur in any particular order.

It should be noted that the presence of a working electrode results in measurement of analyte concentration, which may interfere with the control solution reading. Thus, in one embodiment, the subject method involves "deactivating" the glucose signal so that the measured signal of the control solution is glucose-independent. This may be accomplished by temporarily disconnecting the working electrode.

It should be emphasized that accurate measurements of concentration levels in a bodily fluid, such as blood, may be critical to the long-term health of many users. As a result, there is a need for a high level of reliability in the meters and test strips used to repeatedly measure concentration levels in fluids. It is therefore desirable to have a cost effective auto-calibration system for diagnostic test strips that more reliably and more accurately provides an average glucose reading. For the same reason, it would be highly beneficial for electrochemical biosensors, and glucose monitoring systems in particular, to accurately, automatically and rapidly distinguish between control and sample solutions.

SUMMARY

Embodiments of the invention include methods for automatic discrimination of sample from control or standard solutions; specially formulated control or standard solutions that enable automatic sample discrimination; and devices and systems used to determine constituent levels within fluids that employ such automatic sample discrimination methods or specially formulated solutions.

In one embodiment the invention provides a method of automatically discriminating a sample solution from control solution, comprising introducing a sample or control solution into an electrochemical biosensor. The biosensor typically comprises one or more non-working electrodes or traces, at least one working electrode, and at least one enzyme reagent. The method also comprises applying a voltage between any pair of electrodes, measuring the current, and automatically identifying the sample or control solutions based on the current value.

In a further embodiment, the subject method involves two separate measurements, which need not occur in any particular sequence. The two measurements are performed under different conditions. Each measurement involves a discrete voltage and a discrete electrode configuration. By way of example, a first measurement involves quantitatively determining the concentration of an analyte in a sample wherein a relatively low voltage is applied across one working and one non-working electrode. The concentration of an analyte in the solution, such as glucose, is recorded. A separate measurement is performed to qualitatively determine the fluid conductivity in the presence of a control solution identifier wherein a relatively high voltage is applied across two non-working electrodes.

The conductivity of the control solution may be based on the presence of a control solution identifier, such as sodium chloride (or any other salt that will not be detected under the regular glucose measurement condition but does change the bulk solution conductivity). The above two measurements may not occur in this particular sequence. For example, the first step could involve applying a relatively high voltage across two non-working electrodes to determine the conductivity of a solution based on a control solution identifier such as NaCl. The second step could then involve applying a relatively low voltage is across one working and one non-working electrode to quantitatively determine the concentration of an analyte in the solution, such as glucose.

In a specific embodiment, ascorbic acid is added to a control solution. A meter applies a voltage of 100 mV across a working and a non-working electrode and measures and records the concentration of glucose in a sample solution. The meter then raises the voltage to between about 400 mV and 500 mV and applies said voltage across two non-working electrodes. The meter then measures and records the bulk conductivity of the sample and control solutions. The presence of ascorbic acid in the control solution causes it to appear identifiably different from sample due to a significant difference in conductivity between the two fluids. A calculation is then performed by the meter based on the measured current and conductivity to determine whether the fluid is a biological fluid sample or a control solution.

In a related embodiment, the claimed method involves applying a voltage between two non-working electrodes to measure electron conductivity in a fluid. The fluid may derive from a control or standard solution, or a sample with analytes of interest therein. The method may further involve deactivating the glucose signal so that the measured signal of the control solution is glucose-independent. Such a method may involve disconnecting the working electrode so that electrons temporarily flow between two non-working electrodes.

A control solution is generally an aqueous solution that contains a known amount of analyte, such as glucose. Another aspect of the claimed subject matter is that a control solution "identification agent" or control solution "identifier" is added to the control solution Said control solution "identification agent" or control solution "identifier" may be, but is not limited to sodium chloride, potassium chloride, uric acid, or ascorbic acid, for example. The identification agent causes the control solution to appear identifiably different from the sample measured due to a significant difference between the conductivity or other measurable properties of the two fluids.

BRIEF DESCRIPTION OF THE DRAWINGS

Aspects and embodiments of the claimed subject matter are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. The drawings, however, should not be construed as limiting the scope of the claimed subject matter. All literature citations are incorporated herein by reference in their entirety. Included in the drawings are the following figures:

DETAILED DESCRIPTION OF THE PREFERRED EMBODIMENTS

Figure 1:
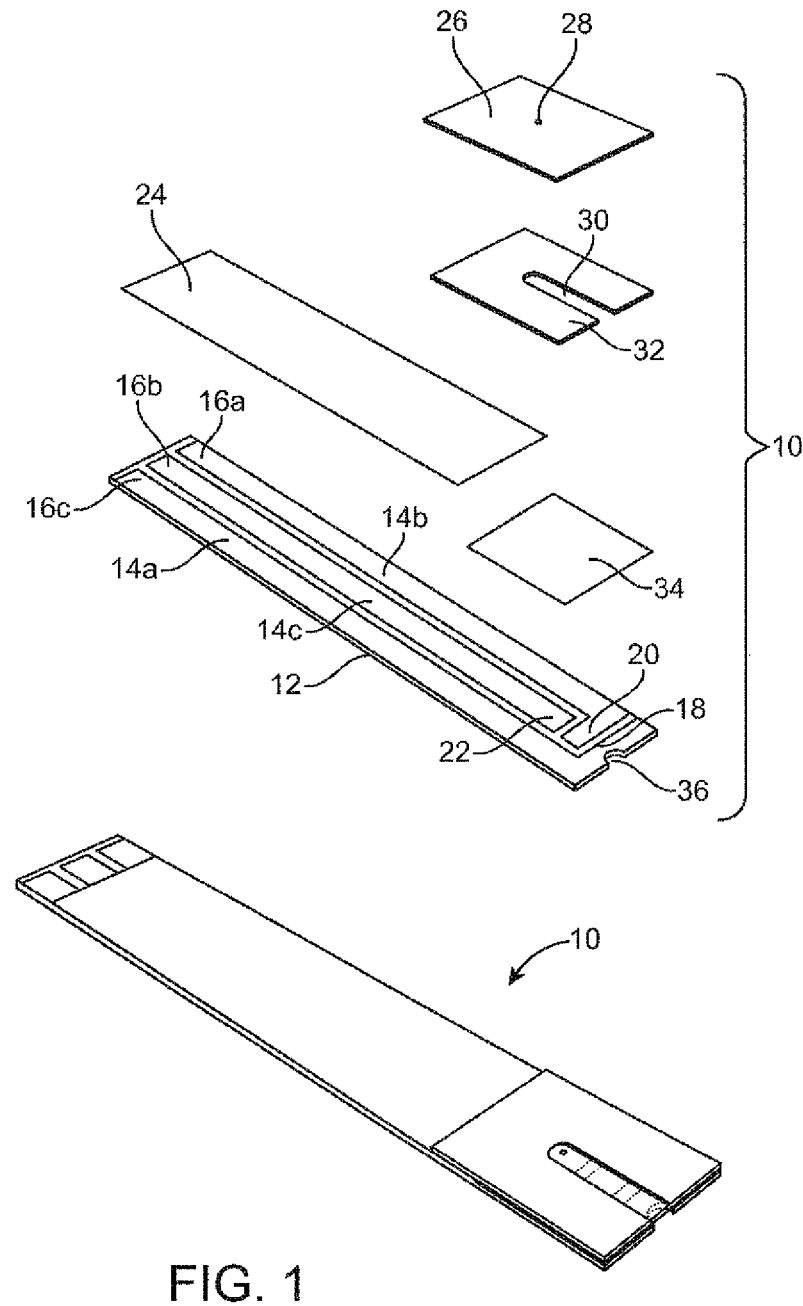
FIG. 1 is a schematic diagram that illustrates a perspective view of a biamperometric strip containing a combined working/reference layer.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor designs or usages, unless implicitly or explicitly understood or stated otherwise, as such may vary.

The terms "amperometry" and "amperometrically" refer to the measurement of the strength of a current and include steady-state amperometry, chronoamperometry, and Cottrell-type measurements.

The term "bodily fluid" in the context of the invention encompasses all non-blood bodily fluid that can be found in the soft tissue of an individual's body, such as subcutaneous, dermal, or interstitial tissue, in which the analyte may be measured. By way of example, the term "bodily fluid" encompasses a fluid such as dermal, subcutaneous, or interstitial fluid.

The term "blood" in the context of the invention encompasses whole blood and its cell-free components, such as plasma and serum. The term "capillary blood" refers to blood that is associated with any blood-carrying capillary of the body.

The term "concentration" may refer to a signal that is indicative of a concentration of an analyte in a medium, such as a current signal, for example, to a more typical indication of a concentration of an analyte in a medium, such as mass of the analyte per unit volume of the medium, for example, or the like.

"Conductivity" or "electrical conductivity" is a measure of a material's ability to conduct an electric current at a defined temperature and a defined phase. The material may be a fluid or a bodily fluid. Conductivity may also be defined as the ratio of current density to electric field strength. Conductivity is the reciprocal (inverse) of electrical resistivity and has the SI units of siemens per meter (S·m−1).

"Coulometry" refers to the determination of charge passed or projected to pass during complete or nearly complete electrolysis of a compound, either directly on the electrode or through one or more electron-transfer agents. The charge is determined by measurement of electrical charge passed during partial or nearly complete electrolysis of the compound or, more often, by multiple measurements during the electrolysis of a decaying current over an elapsed period. The decaying current results from the decline in the concentration of the electrolyzed species caused by the electrolysis.

A "counter electrode" refers to an electrode paired with the working electrode, through which passes a current about equal in magnitude and opposite in sign to the current passing through the working electrode. In the context of the invention, the term "counter electrode" is meant to include counter electrodes which also function as reference electrodes (i.e., a counter/reference electrode). The term "reference electrode" includes both a) reference electrodes and b) reference electrodes that also function as counter electrodes (i.e., counter/reference electrodes), unless otherwise indicated. The term "counter electrode" includes both a) counter electrodes and b) counter electrodes that also function as reference electrodes (i.e., counter/reference electrodes), unless otherwise indicated.

The counter electrode and/or reference electrode may be formed on the substrate or may be separate. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852.

The working electrode or electrodes are formed using conductive traces disposed on the substrate. The counter electrode and/or reference electrode, as well as other optional portions of the sensor, such as a temperature probe, may also be formed using conductive traces disposed on the substrate. These conductive traces may be formed over a smooth surface of the substrate or within channels formed by, for example, embossing, indenting or otherwise creating a depression in the substrate.

In some embodiments of glucose measurement by a biosensor, the counter electrode is where electrons exit the sensor and return to the sample fluid.

The term "electrolysis" refers the electro-oxidation or electro-reduction of a compound either directly at an electrode or via one or more electron-transfer agents, such as redox mediators and/or enzymes, for example.

An "immobilized" material refers to a material that is entrapped on a surface or chemically bound to a surface.

An "implantable" device refers to a fully implantable device that is implanted fully within a body and/or an at least partially implantable device that is at least partially implanted within a body. An example of an at least partially implantable sensing device is a transcutaneous sensing device, sometimes referred to as a subcutaneous sensing device, that is associated with a portion that lies outside of a body and a portion that penetrates the skin from the outside of the body and thereby enters the inside of the body.

The term "measure," as in "to measure the concentration," is used herein in its ordinary sense and refers to the act of obtaining an indicator, such as a signal, that may be associated with a value, such as concentration, for example, and to the act of ascertaining a value, such as a concentration, for example. The term "monitor," as in "to monitor the concentration," refers to the act of keeping track of more than one measurement over time, which may be carried out on a systematic, regular, substantially continuous, and/or on-going basis. The terms measure and monitor may be used generally herein, such as alternately, alternatively, or interchangeably, or more specifically, as just described.

The term "measurement" may refer to a signal that is indicative of a concentration of an analyte in a medium, such as a current signal, for example, to a more typical indication of a concentration of an analyte in a medium, such as mass of the analyte per unit volume of the medium, for example, or the like. The term "value" may sometimes be used herein as a term that encompasses the term "measurement."

The term "patient" refers to a living animal, and thus encompasses a living mammal and a living human, for example. The term "subject" may sometimes be used herein as a term that encompasses the term "patient."

The term "redox mediator" refers to an electron-transfer agent that transfers electrons between a compound and a working electrode, either directly or indirectly.

The term "reference electrode" encompasses a reference electrode that also functions as a counter electrode (i.e., a counter/reference electrode), unless the description provides that a "reference electrode" excludes a counter/reference electrode. This electrode serves as a reference point that is used to precisely set the potential (or propensity to accept electrons) of the working electrode.

"Resistivity" refers to a measure of how strongly a material opposes the flow of electric current. The material may be a fluid or a bodily fluid. A low resistivity indicates a material that readily allows the movement of electrical charge. The SI unit of electrical resistivity is the ohm·meter.

The term "working electrode" refers to an electrode at which the analyte, or a compound whose level depends on the level of the analyte, is electro-oxidized or electro-reduced with or without the agency of an electron transfer agent, such as a redox mediator. The working electrode is the electrode through which electrons from a candidate compound such as glucose enter a biosensor.

An aspect of the invention employs methods for measuring the conductivity of sample and control or standard solutions. Such methods typically require that the conductivity measurements are distinct from and do not interfere with the electrochemical measurement of constituents or particular analytes within the sample.

In one embodiment, the invention makes use of a first measurement of current following the application of a desired voltage by a meter or reference electrode, with the result indicating the concentration of a constituent, or particular analyte in a sample solution. This first measurement is followed by a second measurement of current following the application of a desired voltage, with the result indicating the conductivity of sample versus control solutions. For the measurement of particular analytes in a sample solution, voltage is applied between a working and a non-working electrode. For the measurement of conductivity, voltage is applied between two non-working electrodes while the working electrode is temporarily disconnected. Applied voltages typically may differ between the first and second measurements, with the voltage applied for the conductivity measurement typically being higher than the voltage applied for the measurement indicating the concentration of a constituent of the sample. For the measurement of conductivity, preferred voltages are at least about 200 mV, more preferably at least about 300 mV, and most preferably at least about 400 mV. For the measurement of conductivity, current is preferably measured less than about 1 second after application of the desired voltage, more preferably less than about 0.5 seconds after the application of the desired voltage, and most preferably less than about 0.25 seconds after the application of the desired voltage.

An embodiment of the invention makes use of a specially formulated control solution. Such a control solution is formulated so as to alter the control solution's ability to conduct electricity. The formulation of an aqueous control solution with an increased conductivity or lowered resistivity may be accomplished through an increase in the bulk ion concentration, which may be accomplished efficiently by increasing the molar concentration of dissolved salts. An essential feature of such a specially formulated control solution is that the control solution must have a substantially different conductivity than the sample solution, preferably with the control having higher conductivity, lower resistivity and greater bulk ion concentration than the sample. Preferred control solution ion concentrations are preferably greater than about 150 mM, more preferably greater than about 200 mM and most preferably greater than about 250 mM. Any of a number of soluble salts may be used to increase the conductivity of the control solution, such as, for example, chloride salts of sodium, potassium, lithium, or rubidium, as well as uric or ascorbic acid.

By way of example, the invention provides a method whereby an electrochemically active agent, such as the "control solution identifier" of the present invention, is placed into a control solution. The electrochemically active agent requires a different activation voltage than that of the analyte of interest in a sample solution. Upon application of a relatively low voltage, this discrepancy results in only the analyte of interest being activated. This allows one to selectively detect the concentration of the analyte of interest. When the electrode configuration is changed (whereby the working electrode may be optionally disconnected), and a greater voltage is applied across two non-working electrodes, the solution conductivity is detected. Where the magnitude of conductivity is relatively large, the signal is indicative of a control solution. In contrast, where the magnitude of conductivity is relatively small, the signal is indicative of a sample solution.

In a particular embodiment, the electrochemically active agent is sodium chloride and the analyte of interest is glucose. When a low voltage is applied across a working and a non-working electrode, a meter detects a signal from glucose, but not from sodium chloride. Glucose concentration is calculated and recorded. When the working electrode is deactivated, and a voltage is applied across two non-working electrodes, the resulting current is indicative of solution conductivity. The solution conductivity of a control solution should be identifiably greater than that of a sample solution. This discrepancy therefore allows for differentiation between the control and sample solutions.

The methods of the present invention may be particularly useful in connection with a device that is used to measure or monitor an analyte such as glucose. Accordingly, an aspect of the invention is a device that measures the conductivity of sample and control or standard solutions and automatically discriminates between control and sample solutions based on the difference in conductivity measured between sample and control. Such a device preferably also measures the concentration of a constituent in the sample or control solution. Hardware necessary for such measurements typically includes components capable of applying an electrical potential across two non-working electrodes and subsequently measuring the resulting current within a desired time window and may also include one or more of the following: (1) a calibration device; (2) a mechanism for the storage of results in computer memory; (3) a mechanism for visual, auditory or other convenient methods of displaying the results; and (4) a mechanism for wired or wireless transmission of the results from the measurement device to another device for subsequent storage, evaluation, recalculation, retransmission or display. The device may or may not be in good contact, such as thorough and substantially continuous contact, with the sample.

Software necessary for conductivity measurements and for subsequent automatic discrimination typically includes one or more cycles that include the logical steps of (1) initiating a desired electrical potential (2) waiting a desired period of time (3) measuring the resulting current (4) calculating the conductivity using both measured values and device-specific values (5) comparing these results to a range of expected values for sample and control solutions.

An aspect of the invention also includes a system or a kit that measures the conductivity of sample and control or standard solutions, automatically discriminates between control and sample solutions, and records, transmits, communicates or otherwise displays this determination. Such a system preferably also measures the concentration of a constituent in the sample or control solution. Hardware necessary for such measurements typically includes components capable of applying an electrical potential across two non-working electrodes and subsequently measuring the resulting current within a desired time window and may also include one or more of the following: (1) a calibration device; (2) a mechanism for the storage of results in computer memory; (3) a mechanism for visual, auditory or other convenient methods of displaying the results; and (4) a mechanism for wired or wireless transmission of the results from the measurement device to another device for subsequent storage, evaluation, recalculation, retransmission or display.

Software necessary for conductivity measurements and for subsequent automatic discrimination typically includes one or more cycles that include the logical steps of (1) initiating a desired electrical potential (2) waiting a desired period of time (3) measuring the resulting current (4) calculating the conductivity using both measured values and device-specific values (5) comparing these results to a range of expected values for sample and control solutions (6) and recording, displaying or transmitting results that include the determination of sample or control.

An aspect of the invention is directed to highly reliable and rapid automatic discrimination of sample from control solutions that apply across a range of effective temperatures. Given the temperature dependence of the conductivity of aqueous solutions, control solutions will be formulated to achieve substantially different conductivity than the sample solution and will allow for highly reliable discrimination across a substantially wide range of effective temperatures. Because reliable discrimination is also a function of the voltage applied by the measurement device, a suitable voltage will also be selected that achieves highly reliable discrimination across a substantially wide range of temperatures. Preferably, automatic sample discrimination will be highly reliable across a range of temperatures between about 20 and about 30° C., more preferably across a range of temperatures between about 15 and about 35° C. and most preferably across a range of temperatures between about 4 and about 40° C. For the purposes of automatic sample discrimination, highly reliable discrimination is preferably a measurement difference of at least one standard deviation above and below the control and sample solutions, more preferably a measurement difference of at least two standard deviations above and below the control and sample solutions, and most preferably a measurement difference of at least three standard deviations above and below the control and sample solutions.

An aspect of the invention is directed to highly reliable and automatic discrimination of sample from control solutions in the context of measurements in the presence of analytes that may introduce substantial variations in electrochemical measurements. Given that variations in the hematocrit of blood samples often results in a bias in the measurement of glucose concentration.

Preferably, automatic sample discrimination will be highly reliable for blood samples with a hematocrit value less than about 50%, more preferably for blood samples with a hematocrit value less than about 30% and most preferably for blood samples with a hematocrit value less than about 20%. For the purposes of automatic sample discrimination, highly reliable discrimination is preferably a measurement difference of at least one standard deviation above and below the control and sample solutions, more preferably a measurement difference of at least two standard deviations above and below the control and sample solutions, and most preferably a measurement difference of at least three standard deviations above and below the control and sample solutions In one particular embodiment, the invention is directed to the automatic detection of control solution in the measurement of blood glucose using a diagnostic test strip. In such an embodiment, the test strip comprises an electrically insulating base layer, a conductive pattern formed on the base layer providing at least one electrode disposed on the base layer at a proximal region of the strip, electrical strip contacts disposed on the base layer at a distal region of the strip, conductive traces electrically connecting the electrodes to at least some of the electrical strip contacts, and a distinct distal conductive region provided distal to the electrical strip contacts. A reagent layer contacts at least a portion of at least one electrode and an electrically insulating material includes a pattern of apertures. The electrically insulating material is disposed over at least a portion of the distal conductive region such that the apertures expose a pattern of the underlying distal conductive region to at least partially form a distinct pattern readable to identify data particular to the test strip.

Figure 2:
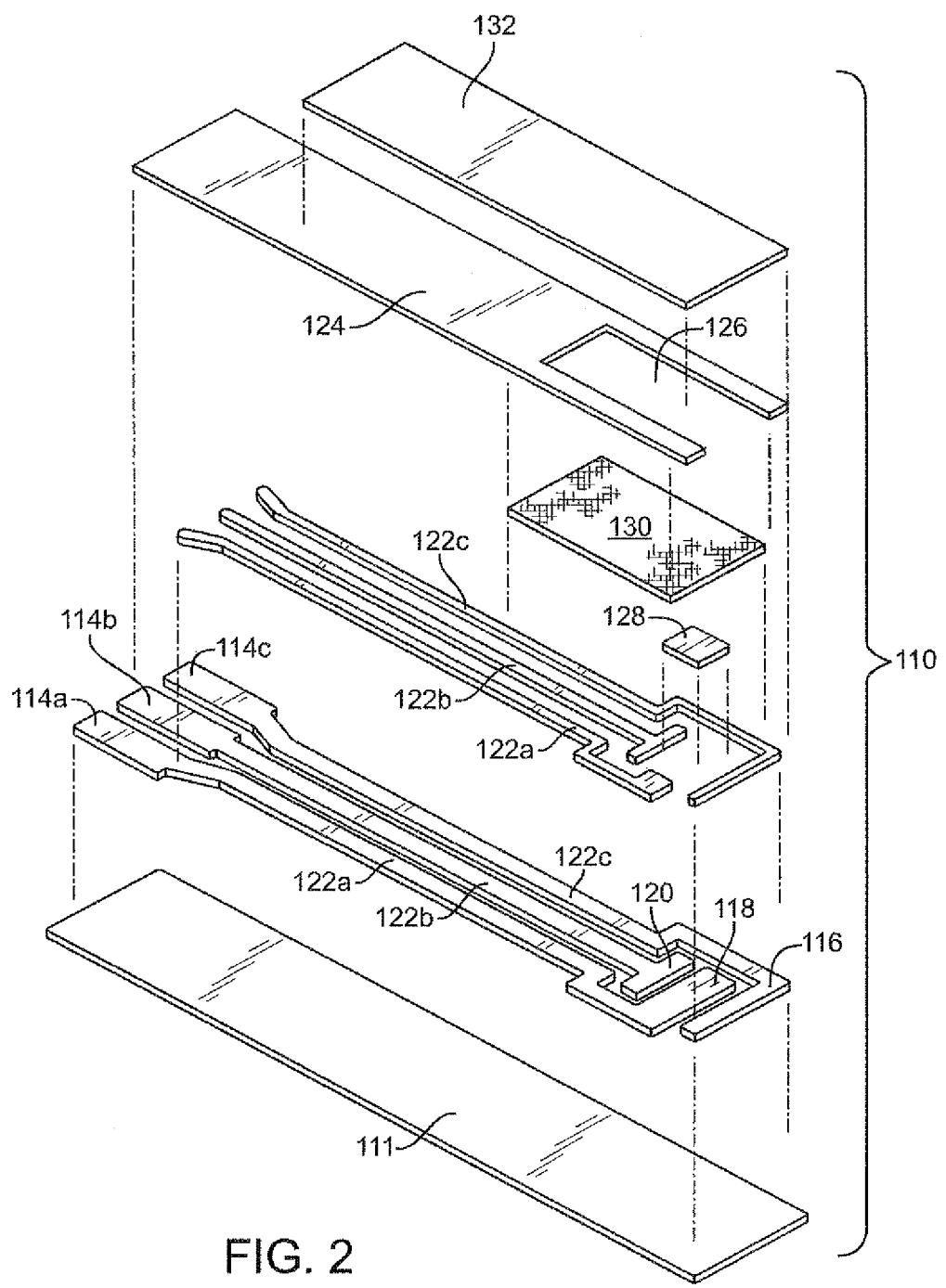
FIG. 2 is a schematic diagram that illustrates a perspective view of a standard amperometric strip with separate working and reference layers.
Figure 3:
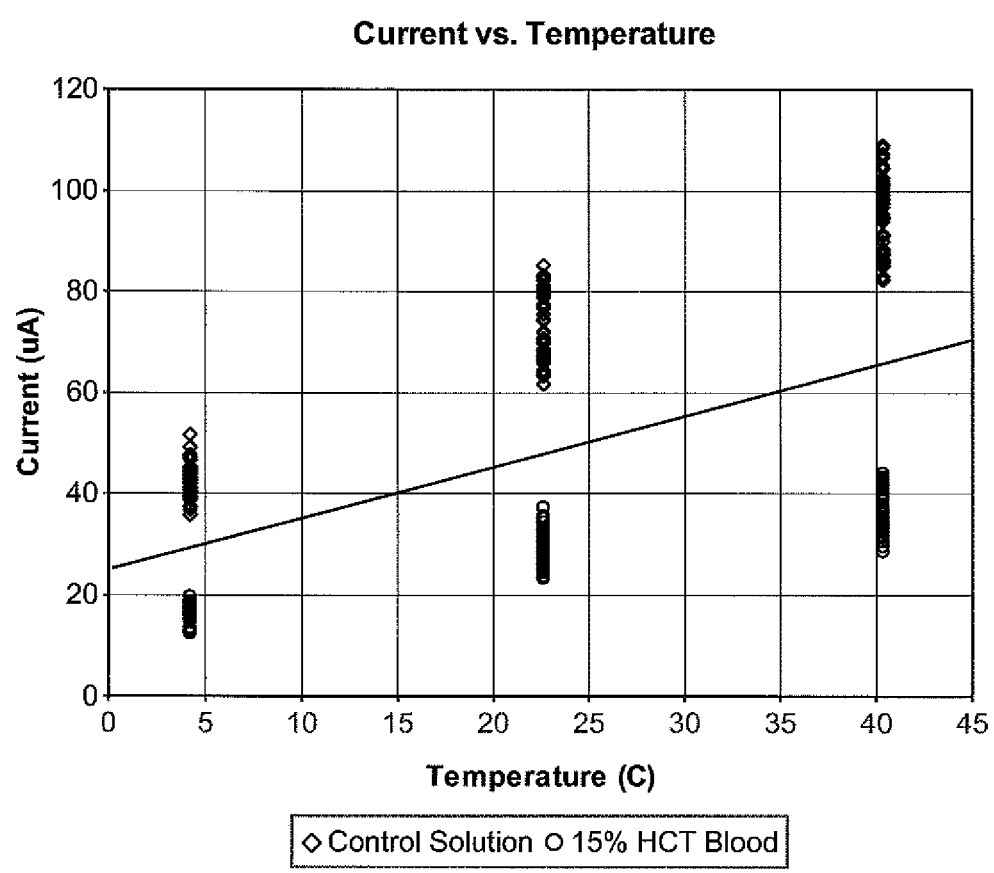
FIG. 3 depicts a plot of electrical current measured for modified glucose monitoring control solutions (upper, square icons) and 15% hematocrit blood samples (lower, circle icons) at three different temperatures. The plot shows the clear separation of current measured in control solutions and blood samples. The experiment was conducted at three different temperatures: 4.2° C., 23° C. (room temperature), and 40° C. Current was measured for control solutions and blood samples after a potential difference of 400 mV was applied. Three different lots of FREESTYLE blood glucose monitoring system glucose biosensors were tested. Two different control solutions were tested: a high-glucose control (about 400 mg/dl) and a low-glucose control (about 50 mg/dl). The ionic strength of all control solutions was adjusted by adding NaCl to a final concentration of about 300 mM. Blood samples with a 15% hematocrit value were used.
Figure 4:
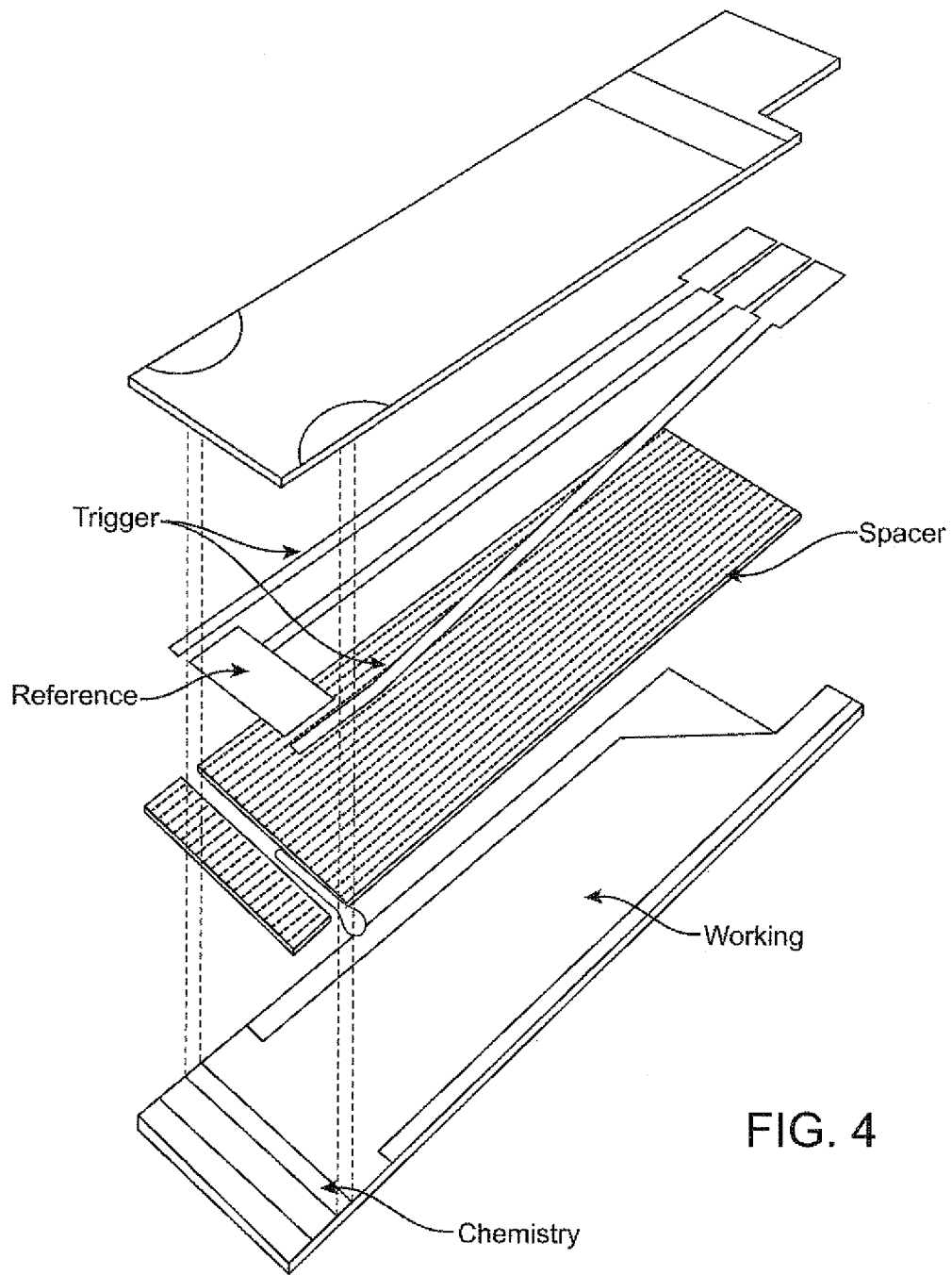
FIG. 4 is a schematic diagram that illustrates a perspective view of a coulometric strip with working and non-working electrodes on separate substrates.

Biosensor strips suitable for aspects of the invention are illustrated in FIGS. 1 and 2. Referring now to FIG. 1, a biamperometric strip 10 is shown having a combined working/reference layer. In a preferred embodiment, the strip comprises a patterned gold electrode substrate 12, e.g., a thin (~50 nm) gold layer deposited on an insulating polymer substrate, usually polyester (an electrode design or artwork of tracks and electrodes is then formed by removing gold in selected regions by such methods as laser ablation, chemical etching, etc.). The substrate 12 supports three tracks 14a, 14b, and 14c of electrically conductive gold. In another embodiment, the substrate 12 comprises only an insulating polymer substrate, usually polyester, and then an electrode design or artwork of tracks and electrodes is formed by printing a conducting ink, e.g., including carbon. The substrate 12 then supports three tracks 14a, 14b, and 14c of electrically conductive ink, e.g., including carbon. The tracks 14a, 14b, and 14c determine the positions of electrical contacts 16a, 16b, and 16c, a reference electrode 18, a working electrode 20, and a counter/start control electrode 22. The electrical contacts 16a, 16b, and 16c can be inserted into an appropriate measurement device (such as a meter receiving port) for measurement of current by making electrical contact with the internal electronics of a meter, for example.

Each of the elongated portions of the conductive tracks 14a, 14b, and 14c can optionally be overlaid with an opaque tape layer 24 which comprises a polymer film with an adhesive coating on the lower surface. The adhesive is preferably a pressure-sensitive adhesive (PSA). The upper surface may be decorated/printed with designs, logos, graphics, trademarks, identifiers, etc. Alternatively, the tape may be transparent and the decoration is printed on the lower surface, followed by an opaque printed layer, then finally the PSA layer. The prime function is as an insulator and protecting layer to prevent short-circuiting of the electrode tracks by biological sample and to protect the electrode tracks from damage, such as scratching.

Optionally, a cover layer 26 defining the upper boundary of the sample chamber for biological sample can overlay the opaque tape layer 24. The cover layer is made of a thin polymer tape, preferably polyester. The upper surface of the cover layer may be coated with a hydrophobic coating such that it is wetted poorly by the biological sample. The lower surface of the cover layer is coated with a hydrophilic coating, which may contain surfactants to promote filling of the biological sample into the sample chamber. The cover layer 26 is preferably transparent such that the progress of sample filling into the sample chamber can be monitored visually. This is a useful visual check that the sample chamber has filled completely.

A breather hole 28 functions to allow the release of air displaced from the sample chamber 30 by the ingress of biological sample. The sample chamber would not fill without this breather hole. The hole is preferably formed in the cover layer by the action of a laser and is aligned with the rear end of the sample chamber above the counter/start control electrode 22.

A spacer layer 32 comprises a thin (~100 μm) polymer tape layer with pressure-sensitive adhesive (PSA) on both surfaces. The spacer layer functions to define the dimensions (height and surface area) and shape of the sample chamber 30. The spacer layer confines the biological sample within the sample chamber and defines the area of the reagent layer 34 that is exposed to the biological sample. Optionally the spacer layer is colored to provide contrast between itself 32, the reagent layer 34 and the biological sample. In one embodiment, the spacer layer 32 and the cover 26 layer is contained within a pre-formed capillary sub-assembly and contains no mesh.

A reagent layer 34 comprises thin (~5 μm) film of active reagents (enzyme, redox mediator, cofactor), polymer film-former, additives, stabilizers, etc. Said reagent layer functions to act on the analyte of interest in the biological sample to provide a signal (proportional to the concentration of analyte) which translates to an electrical current in the electrode tracks. In one embodiment, said reagent layer 34 spans the whole width of the electrode strip covering all electrode tracks. A redox mediator may also be used as the reference redox couple for the reference electrode 18. In one embodiment, this layer is a combined working and reference layer.

A biological sample application/receiving area 36 may in one embodiment be a notch cut in the end of the electrode strip to identify to the user the point at which the biological sample should be applied. This receiving area 36 may also define the entrance to the sample chamber and promote ingress of the sample into the chamber.

The working electrode 20 includes a layer of conductive material containing a working area 20a. The working area 20a may be formed from a reagent composition, which is added (e.g., printed) on the layer of conductive material of the working electrode 20. The reagent composition includes a mixture of an oxidation-reduction mediator, a metal ion, a counter anion, an enzyme, and, optionally, a conductive material.

The working area 20 may be overlaid with reagent layer 34 derived from a printing ink or coating solution that includes the reagent composition described above, that includes a mixture of an enzyme, an oxidation-reduction mediator, a counter anion, a metal ion, and, optionally, a conductive material though short-circuits must be prevented. Alternatively, instead of an enzyme, the working area 20 can contain a substrate that is catalytically reactive with an enzyme to be assayed. The reagent composition is then applied in a single step to the working electrode area 20, counter electrode area 22 and the reference electrode area 18 as a single area of fixed length.

In other embodiments, the electrodes are formed on one or more electrode supports by any suitable method including chemical etching, laser ablation, photolithography, and the like. In general, the electrode support is formed from an insulating material, so that it will not provide an electrical connection between the electrodes of the electrode set. Examples include glass, ceramics and polymers. In certain embodiments, the electrode substrate is a flexible polymer, such as a polyester or polyimide.

For example, in the laser ablation process, the metallic layer may be ablated into an electrode pattern. Furthermore the patterned metallic layer may be coated or plated with additional metal layers. For example, the metallic layer may be copper, which is then ablated with a laser, into an electrode pattern; subsequently, the copper may be plated with a titanium/tungsten layer, and then a gold layer, to form the desired electrodes. In certain embodiments, however, only a single layer of gold is used, which is directly in contact with the electrode substrate. In such embodiments, the reagent composition can be positioned adjacent to the electrode(s).

In one such method, one or more channels are formed in the substrate, for example by an embossing process using an embossing die or roller. Other methods for forming the channels, such as the use of a laser, or photolithography and etching of the substrate can also be employed if desired.

The conductive material may contain pure metals or alloys, or other materials which are metallic conductors. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. In certain embodiments, the conductive material includes carbon, gold, platinum, palladium, iridium, or alloys of these metals, since such noble metals and their alloys are unreactive in biological systems.

The reagent composition includes an aqueous solution of, a redox mediator, a coordinating metal ion and its counter anion, as well as a stabilizing metal ion and its counter anion. For the working electrode 20, the reagent composition also includes an enzyme. For example, when the analyte to be measured is glucose in blood, the enzyme is glucose-responsive, such as glucose dehydrogenase or glucose oxidase, while the redox mediator may be a 1,10-phenanthroline-5,6-dione. In the alternative, for the working electrode 20, the printing ink can include a substrate in lieu of an enzyme when the analyte to be measured is an enzyme.

In certain embodiments, the reagent composition can be screen-printed. In such embodiments, the reagent composition can further include a polysaccharide (e.g., a guar gum or an alginate), a hydrolyzed gelatin, an enzyme stabilizer (e.g., glutamate or trehalose), a film-forming polymer (e.g., a polyvinyl alcohol), a defoaming agent, a buffer, or a combination of the foregoing.

The electrodes cannot be spaced so far apart that the working electrode 20, the counter electrode 22 and the reference electrode 18 cannot be covered by the sample. In certain embodiments, the length of the path to be traversed by the sample (i.e., the sample path) is kept as short as possible in order to minimize the volume of sample required. The maximum length of the sample path can be as great as the length of the biosensor strip. However, the corresponding increase in resistance of the sample limits the length of the sample path to a distance that allows the necessary response current to be generated. The resistance of the sample is also influenced by the distance from the edge of the area of the reference electrode 18 and counter electrode 22 to the edge of the working area of the working electrode 20. Positioning the electrodes contiguously is conventional.

The counter/start control electrode 22 can be placed downstream of the reference electrode. The counter/start control electrode 22 can be used to determine when the sample has been applied to the strip, thereby activating the assay protocol (see, e.g., U.S. Ser. No. 09/529,617, filed Jun. 7, 2000, now U.S. Pat. No. 6,736,957, the disclosure of which is incorporated herein by reference in its entirety).

A standard amperometric strip 110 with separate working and reference layers suitable for aspects of the invention is illustrated in FIG. 2. Referring now to FIG. 2, an electrode support 111, such as an elongated strip of polymeric material (e.g., polyvinyl chloride, polycarbonate, polyester, or the like) supports three tracks 112a, 112b, and 112c of electrically conductive ink, such as carbon. These tracks 112a, 112b, and 112c determine the positions of electrical contacts 114a, 114b, and 114c, a reference electrode 116, a working electrode 118, and a counter electrode 120. The electrical contacts 114a, 114b, and 114c are insertable into an appropriate measurement device (not shown) for measurement of current.

Each of the elongated portions of the conductive tracks 112a, 112b, and 112c can optionally be overlaid with a track 122a, 122b, and 122c of conductive material, for example made of a mixture including silver particles and silver chloride particles. The enlarged exposed area of track 122b overlies the reference electrode 116. A layer of a hydrophobic electrically insulating material 124 further overlies the tracks 112a, 112b, and 112c. The positions of the reference electrode 116, the working electrode 118, the counter electrode 120, and the electrical contacts 114a, 114b, and 114c are not covered by the layer of hydrophobic electrically insulating material 124. This hydrophobic electrically insulating material 124 serves to prevent short circuits. The layer of hydrophobic electrically insulating material 124 has an end-fill opening 126 formed therein. This opening 126 provides the boundary for the reaction zone of the biosensor strip 110. Because this insulating material is hydrophobic, it can cause the sample to be restricted to the portions of the electrodes in the reaction zone. The working electrode 118 comprises a layer of a non-reactive electrically conductive material on which is deposited a layer 128 containing a reagent composition for carrying out an oxidation-reduction reaction. At least one layer of mesh 130 overlies the electrodes. This layer of mesh 130 protects the printed components from physical damage. The layer of mesh 130 also helps the sample to wet the electrodes by reducing the surface tension of the sample, thereby allowing it to spread evenly over the electrodes. A cover 132 encloses the surfaces of the electrodes that are not in contact with the electrode support 111. This cover 132 is a liquid impermeable membrane.

The reagent composition 128 is deposited on that portion of the electrically conductive material of the working electrode 118 where the oxidation-reduction reaction is to take place when a sample is introduced to the biosensor strip 110. In such embodiments, the reagent composition 128 can be applied to the working electrode 118 as a discrete area having a fixed length. Typical analytes of interest include, for example, glucose and ketone bodies. Typical non-reactive electrically conductive materials include, for example, carbon, platinum, palladium, iridium, and gold. A semiconducting material such as indium doped tin oxide can be used as the non-reactive electrically conductive material. In certain embodiments, the reagent composition includes a mixture of an oxidation-reduction mediator and an enzyme. Alternatively, instead of an enzyme, the reagent composition can contain a substrate that is catalytically reactive with an enzyme to be assayed. In the biosensor strips of aspects of the invention, the reagent(s) are applied in the form of a composition containing particulate material and having binder(s), and, accordingly, does not dissolve rapidly when subjected to the sample. In view of this feature, the oxidation-reduction reaction will occur at the interface of working electrode 118 and the sample. The glucose molecules diffuse to the surface of the working electrode 118 and react with the enzyme/mediator mixture.

In addition to being applied to the working electrode 118, a layer of the reagent composition can be applied to any of the other electrodes, such as the reference electrode when desired, as a discrete area having a fixed length.

Other possible biosensor strip designs include those in which the mesh layer 130 is eliminated, and the flow channel is of such dimensions that the biosensor strip takes up a liquid sample by capillary attraction. See U.S. patent application Ser. No. 10/062,313, filed Feb. 1, 2002, incorporated herein by reference in its entirety.

EXPERIMENTAL

The following examples are put forth so as to provide those of ordinary skill in the art with a complete disclosure and description of how to make and use aspects and embodiments of the present invention, and are not intended to limit the scope of what the inventors regard as the claimed subject matter nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Temperature-Dependence of Automated Sample Discrimination Using a Modified Conductivity Control Solution A blood glucose monitoring system was tested for the ability to rapidly and reliably distinguish between a blood sample and modified control solutions. The experiment was conducted at three different temperatures, and the current measured for control solutions and blood samples. Three different lots of glucose biosensors were tested. Two different control solutions were tested: a high-glucose control (about 400 mg/dl) and a low-glucose control (about 50 mg/dl). The ionic strength of all control solutions was adjusted by adding NaCl to a final concentration of about 300 mM. Blood samples with a 15% hematocrit value were used. A potential difference of 400 mV was applied before the conductivity measurement. Tests were conducted at a range of temperatures, from 4.2° C. to 40° C. The results shown in FIG. 1 indicate that the current measured in the sample and the modified control solution have a clear separation between sample and control, and the sample and control can potentially be automatically discriminated for a large number of blood samples and test strip lots tested at a wide range of temperatures. An independent temperature measurement by the meter can be used to improve the accuracy of sample type identification.

The preceding merely illustrates principles of various aspects of the invention. It is also to be understood that the following claims are intended to cover all of the generic and specific features of the invention as described herein, and all statements of the scope of the invention which, as a matter of language, might be said to fall there between. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the claimed subject matter as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the presently claimed subject matter, therefore, is not intended to be limited to the exemplary embodiments shown and described herein. Rather, the scope and spirit of the presently claimed subject matter is embodied by the appended claims.

That which is claimed is:

1. A method of measuring one or more analytes in a fluid, comprising:

introducing a biological fluid sample or control solution into an electrochemical biosensor having a working electrode and two or more electrodes selected from the group consisting of a reference electrode, counter electrode, trigger electrode and dummy electrode;

applying a first voltage across the working electrode and a first electrode selected from the group consisting of a reference electrode, counter electrode, trigger electrode and dummy electrode and obtaining a first measurement;

applying a second voltage across the first electrode and a second electrode selected from the group consisting of a reference electrode, counter electrode, trigger electrode and dummy electrode and obtaining a second measurement;

wherein the first measurement measures an analyte-dependent signal and the second measurement measures a control solution-dependent signal; and obtaining a reading of the fluid conductivity; and calculating the current to determine whether the fluid is a biological fluid sample or a control solution.

2. The method of claim 1 wherein the first voltage applied precedes measurement of an analyte and the second voltage applied precedes measurement of the conductivity of the solution.

3. The method of claim 1 wherein the second voltage applied is greater than the first voltage applied.

4. The method of claim 1 wherein the second voltage applied is at least 50 mV.

5. The method of claim 1 wherein the second voltage applied is at least 400 mV.

6. The method of claim 1 wherein the voltage applied preceding the measurement of the analyte is applied across a different pair of electrodes than the voltage applied preceding the measurement of the conductivity of the solution.

7. A control solution for use in the method of claim 1, wherein said control solution has a substantially different ionic strength than that in a sample solution.

8. The control solution of claim 7 wherein the ionic strength is at least about 200 mM, 400 mM, or 600 mM.

9. The control solution of claim 7 wherein addition of a chloride salt is used to increase the ionic strength.

10. The control solution of claim 9 wherein the chloride salt is sodium chloride.

11. A method for automatically discriminating a sample solution from control solution, comprising:

introducing a sample or control solution into an electrochemical biosensor, said biosensor comprising two or more electrodes selected from the group consisting of a reference electrode, counter electrode, trigger electrode and dummy electrode or traces, at least one working electrode, and at least one enzyme reagent;

applying a first voltage between the working electrode and any one of the two or more electrodes selected from the group consisting of a reference electrode, counter electrode, trigger electrode and dummy electrode;

measuring a first current resulting from the first applied voltage;

applying a second voltage between two of the electrodes selected from the group consisting of a reference electrode, counter electrode, trigger electrode and dummy electrode;

measuring a second current resulting from the second applied voltage; and automatically identifying the sample or control solutions based on the current values.

12. The method of claim 11 wherein the enzyme reagent is deposited onto the working electrode.

13. The method of claim 11 wherein the voltage is applied by a measurement device.

14. The method of claim 11 wherein the current is measured by a measurement device.

15. The method of claim 11 wherein an identifying device automatically identifies the sample or control solutions based on the current values.

16. The method of claim 15, wherein the measurement device measures the concentration of an analyte in a sample solution.

17. The method of claim 16, wherein the sample solution comprises an electrochemically active agent.

18. The method of claim 17, wherein the electrochemically active agent is selected from the group consisting of glucose and ketones.

19. The method of claim 11 wherein the second voltage applied is at least 50 mV.

20. The method of claim 11 wherein the second voltage applied is at least 400 mV.

21. The method of claim 11, wherein said non-working electrodes or traces comprise a conductive metal.

22. The method of claim 11, wherein said electrodes or traces selected from the group consisting of a reference electrode, counter electrode, trigger electrode and dummy electrode comprise Ag/AgCl.

23. The method of claim 11, wherein said first current is temperature dependent and a measured temperature value is used in the step of said identifying the sample or control solution.

24. The method of claim 11, wherein said working electrode is disconnected during the step of measuring said second current.

25. The method of claim 11, wherein the step of automatically discriminating a sample solution from control solution is initiated before or after an analyte determination.

26. A control solution for use in the method of claim 11, wherein said control solution has a substantially different conductivity than that in a sample solution.

27. The control solution of claim 26, wherein the conductivity is substantially higher than that in the sample solution.

* * * * *